United States Patent
DeLuca et al.

(10) Patent No.: US 6,844,461 B2
(45) Date of Patent: Jan. 18, 2005

(54) SYNTHESIS OF A-RING SYNTHON OF 19-NOR-1α,25-DIHYDROXYVITAMIN D₃ FROM (D)-GLUCOSE

(75) Inventors: Hector F. DeLuca, Deerfield, WI (US); Masato Shimizu, Sinagawa-ku (JP); Sachiko Yamada, Hachioji (JP)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 10/722,858

(22) Filed: Nov. 26, 2003

(65) Prior Publication Data

US 2004/0133026 A1 Jul. 8, 2004

Related U.S. Application Data

(63) Continuation-in-part of application No. 10/205,453, filed on Jul. 25, 2002, now Pat. No. 6,683,219.
(60) Provisional application No. 60/308,716, filed on Jul. 30, 2001.

(51) Int. Cl.⁷ .................................................. C07F 7/08
(52) U.S. Cl. ..................... 556/445; 556/400; 568/626; 568/659; 568/660
(58) Field of Search .................. 556/445, 400; 568/626, 659, 660

(56) References Cited

U.S. PATENT DOCUMENTS

| | | | |
|---|---|---|---|
| 5,086,191 A | 2/1992 | DeLuca et al. | |
| 5,581,006 A | 12/1996 | DeLuca et al. | |
| 5,936,133 A | 8/1999 | Deluca et al. | |
| 6,683,219 B2 * | 1/2004 | DeLuca et al. | ............ 568/15 |

OTHER PUBLICATIONS

CA:129:175887 abs of Tetrahedron Lett by Schmitt et al 39(27) p4817–4820 1998.*
CA:139:53208 abs of Bioorganic and Medicinal Chem Letters by Yoshinori et al 13(5) pp 809–812 2003.*
Abstract 122:81736; Sicinski et al; Synthesis and Biological Activity of 2–Hydroxy and 2–Alkoxy Analogs of 1Alpha, 25–Dihydroxy-19–Norvitamin D3; Journal of Medicinal Chemistry; 1994, 37(22), 3730–8.

Abstract 127:359017; Kozikowski et al; Synthesis of 1D–3–Deoxy– and –2,3–Dideoxyphosphatidylinositol; Tetrahedron; 1997, 53(44), 14903–14914.

Abstract 114:7016; Cambie et al; A Stereocontrolled Synthesis of Proto–Quercitol; Australian Journal of Chemistry; 1990, 43(9), 1597–602.

Abstract 115:92747; Baker et al; Design and Synthesis of 6Alpha–Substituted–2Beta–Phosphoryloxycyclohexanes, Potent Inhibitors of Inositol Monophosphatase; Journal of the Chemical Society, Chemical Communications; 1991, (5), 298–300.

Abstract 130:263914; Iwase et al; Bioscience, Biotechnology, and Biochemistry; 1998, 62(12), 2396–2407.

Abstract 96:163074; Yoshikawa et al; Heterocycles, 1982, 17 (Spec. Issue), 209–14.

Sicinski et al; New 1Alpha,25–Dihydroxy–19–Norvitamin D3 Compounds of High Biological Activity: Synthesis and Biological Evaluation of 2–Hydroxymethyl, 2–Methyl, and 2–Methylene Analogues; Journal of Medicinal Chemistry; 1998, (41), 4662–4674.

Posner et al; Stereocontrolled Synthesis of a Trihydroxylated A Ring as an Immediate Precursor to 1Alpha,2Alpha, 25–Trihydroxyvitamin D3; Journal of Organic Chemistry; 1991, (56), 4339–4341.

Perlman et al; 1Alpha,25–Dihydroxy–19–Nor–Vitamin D3, A Novel Vitamin D–Related Compound with Potential Therapeutic Activity; Tetrahedron Letters, 1990, (31), 13, 1823–1824.

Perlman et al; Novel Synthesis of 19–Nor–Vitamin D Compounds; Tetrahedron Letters, 1991, (32), 52, 7663–7666.

* cited by examiner

*Primary Examiner*—Samuel Barts
(74) *Attorney, Agent, or Firm*—Andrus, Sceales, Starke & Sawall, LLP

(57) ABSTRACT

The present invention provides a method for the synthesis of an A-ring synthon phosphine oxide used in the preparation of 19-nor vitamin D compounds, and to novel synthetic intermediates formed during the synthesis. The new method prepares the phosphine oxide from (D)-glucose.

5 Claims, No Drawings

SYNTHESIS OF A-RING SYNTHON OF 19-NOR-1α,25-DIHYDROXYVITAMIN D₃ FROM (D)-GLUCOSE

CROSS-REFERENCE TO RELATED APPLICATIONS

The present application is a continuation-in-part application of U.S. patent application Ser. No. 10/205,453, filed Jul. 25, 2002, and now U.S. Pat. No. 6,683,219, which application is based on and claims priority from provisional patent Application No. 60/308,716 filed on Jul. 30, 2001.

BACKGROUND OF THE INVENTION

The present invention relates to vitamin D compounds, and more particularly to the synthesis of an A-ring synthon used in the preparation of 19-nor vitamin D compounds, and to novel synthetic intermediates formed during the synthesis.

The natural hormone, 1α,25-dihydroxyvitamin $D_3$ and its analog in ergosterol series, i.e. 1α,25-dihydroxyvitamin $D_2$ are known to be highly potent regulators of calcium homeostasis in animals and humans, and their activity in cellular differentiation has also been established, Ostrem et al., Proc. Natl. Acad. Sci. USA, 84, 2610 (1987). Many structural analogs of these metabolites have been prepared and tested, including 1α-hydroxyvitamin $D_3$, 1α-hydroxyvitamin $D_2$, various side chain homologated vitamins and fluorinated analogs. Some of these compounds exhibit an interesting separation of activities in cell differentiation and calcium regulation. This difference in activity may be useful in the treatment of a variety of diseases.

The discovery of the hormonally active form of vitamin $D_3$, 1α,25-dihydroxyvitamin $D_3$ (1α,25-$(OH)_2D_3$ or calcitriol) has greatly stimulated research into its physiology and chemistry. As previously noted, it has been established that 1α,25-$(OH)_2D_3$ not only regulates the mineral metabolism in animals and humans, but also exerts potent effects upon cell proliferation and cellular differentiation. Therefore, the chemistry of vitamin D has been recently focused on the design and synthesis of analogs that can exert selective biological actions.

Recently, a class of vitamin D analogs has been discovered, i.e. the so called 19-nor-vitamin D compounds, which are characterized by the replacement of the A-ring exocyclic methylene group (carbon 19), typical of the vitamin D system, by two hydrogen atoms. Biological testing of such 19-nor-analogs (e.g., 1α,25-dihydroxy-19-nor-vitamin $D_3$) revealed a selective activity profile with high potency in inducing cellular differentiation, and very low calcium mobilizing activity. Thus, these compounds are potentially useful as therapeutic agents for the treatment of malignancies, or the treatment of various skin disorders. Different methods of synthesis of such 19-nor-vitamin D analogs have been described. See for example Perlman et al., Tetrahedron Lett. 31, 1823 (1990); Perlman et al., Tetrahedron Lett. 32, 7663 (1991), DeLuca et al., U.S. Pat. No. 5,086,191, and DeLuca et al U.S. Pat. No. 5,936,133.

In one particularly advantageous method, the preparation of various 19-nor-vitamin D compounds can be accomplished by the condensation of a bicyclic Windaus-Grundmann type ketone having the desired side chain structure with an A-ring phosphine oxide to the corresponding 19-nor vitamin D analog followed by deprotection, particularly at C-1 and C-3 in the latter compounds. One method of preparing the required A-ring phosphine oxides is to transform a methyl ester obtained from quinic acid into the desired A-ring synthon in accordance with the synthesis set forth in DeLuca et al U.S. Pat. No. 5,936,133. It is, however, desirable to provide an alternate method for preparing such A-ring phosphine oxides.

SUMMARY OF THE INVENTION

The present invention provides a new method for the synthesis of an A-ring synthon phosphine oxide used in the preparation of 19-nor vitamin D compounds, and to novel synthetic intermediates formed during the synthesis. The new method prepares the phosphine oxide from (D)-glucose.

The A-ring synthon phosphine oxide to be prepared is represented by the following structure

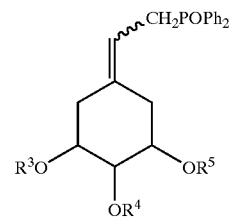

where the wavy line indicates a stereochemical center so that the phosphine oxide substituent may have either the R or S configuration, and may thus be obtained as a mixture of two isomers. Each of $R^3$, $R^4$ and $R^5$ may independently be selected from a hydroxy protecting group, but preferably $R^3$ and $R^5$ are both a t-butyldimethylsilyl hydroxy protecting group (abbreviated "TBS") and $R^4$ is a trimethylsilyl hydroxy protecting group (abbreviated "TMS").

Preferably, the method of making the phosphine oxide comprises the steps of:

converting D-glucose having the structure

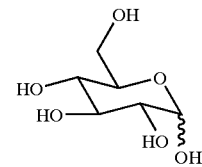

to a 2-deoxy-glucose derivative having the structure

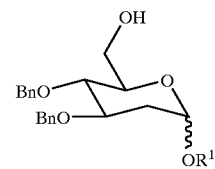

where $R^1$ is an alkyl group;

iodinating the 2-deoxy-glucose derivative to form a 5-iodinated derivative having the structure

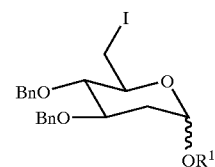

eliminating the iodine substituent of said 5-iodinated derivative to form a 1-ether derivative having the structure

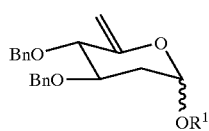

reducing the 1-ether derivative to form a 1-alcohol derivative having the structure

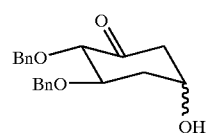

converting the 1-alcohol derivative to a 1-protected derivative having the structure

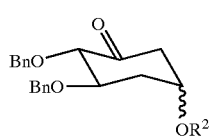

where $R^2$ is a hydroxy protecting group;
reducing the 1-protected derivative with a metal hydride to form a 5-alcohol derivative having the structure

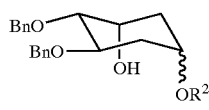

benzylating the 5-alcohol derivative to form a benzylated derivative having the structure

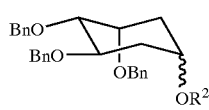

hydrolyzing the benzyl derivative to form a 1-hydroxyl derivative having the structure

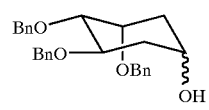

oxidizing the 1-hydroxyl derivative to form a 1-ketone derivative having the structure

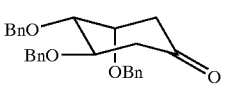

converting the 1-ketone derivative to a 3,4,5-protected derivative having the structure

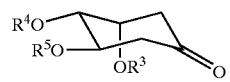

where $R^3$, $R^4$ and $R^5$ are each independently a hydroxy-protecting group;
condensing the 3,4,5-protected derivative to an ester derivative having the structure

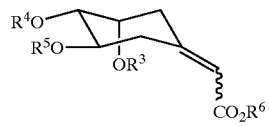

where $R^6$ is an alkyl group;
reducing the ester derivative with a metal hydride to form a 3,4,5-protected-1-alcohol derivative having the structure

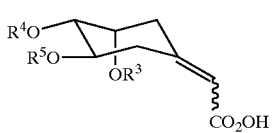

and converting the 3,4,5-protected-1-alcohol to a phosphine oxide having the structure

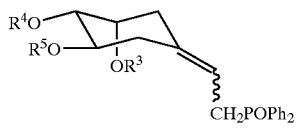

Alternate methods of converting D-glucose to the 2-deoxy-glucose derivative are illustrated in Schemes I and II.

The present invention is also directed toward novel intermediate compounds formed during the method of making the phosphine oxide. One such novel intermediate is the 5-alcohol derivative described in the above process having the following chair configuration:

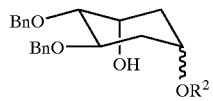

In the above drawing, Bn represents a benzyl group, and $R^2$ is a hydroxy protecting group. This 5-alcohol derivative can also be illustrated by the following Fischer projection drawing:

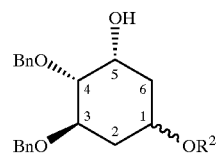

In one particularly preferred form, $R^2$ is a tert-butyldimethylsilyl (TBS) protecting group, and thus the above 5-alcohol derivative may be either compound 15a or 15b in the synthesis illustrated hereinafter as Scheme III. More specifically, compound 15a can be illustrated as follows

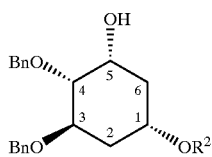

and compound 15b can be illustrated as follows

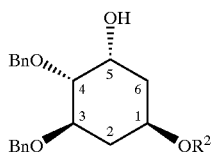

where Bn is a benzyl group and $R^2$ is TBS. However, as noted above, $R^2$ can be any hydroxy-protecting group desired.

DETAILED DESCRIPTION OF THE INVENTION

As used in the description and in the claims, the term "hydroxy-protecting group" signifies any group commonly used for the temporary protection of hydroxy functions, such as for example, alkoxycarbonyl, acyl, alkylsilyl or alkylarylsilyl groups (hereinafter referred to simply as "silyl" groups), and alkoxyalkyl groups. Alkoxycarbonyl protecting groups are alkyl-O—CO— groupings such as methoxycarbonyl, ethoxycarbonyl, propoxycarbonyl, isopropoxycarbonyl, butoxycarbonyl, isobutoxycarbonyl, tert-butoxycarbonyl, benzyloxycarbonyl or allyloxycarbonyl. The term "acyl" signifies an alkanoyl group of 1 to 6 carbons, in all of its isomeric forms, or a carboxyalkanoyl group of 1 to 6 carbons, such as an oxalyl, malonyl, succinyl, glutaryl group, or an aromatic acyl group such as benzoyl, or a halo, nitro or alkyl substituted benzoyl group. The word "alkyl" as used in the description or the claims, denotes a straight-chain or branched alkyl radical of 1 to 10 carbons, in all its isomeric forms. Alkoxyalkyl protecting groups are groupings such as methoxymethyl, ethoxymethyl, methoxyethoxymethyl, or tetrahydrofuranyl and tetrahydropyranyl. Preferred silyl-protecting groups are trimethylsilyl, triethylsilyl, t-butyldimethylsilyl, dibutylmethylsilyl, diphenylmethylsilyl, phenyldimethylsilyl, diphenyl-t-butylsilyl and analogous alkylated silyl radicals. The term "aryl" specifies a phenyl-, or an alkyl-, nitro- or halo-substituted phenyl group.

A "protected hydroxy" group is a hydroxy group derivatised or protected by any of the above groups commonly used for the temporary or permanent protection of hydroxy functions, e.g. the silyl, alkoxyalkyl, acyl or alkoxycarbonyl groups, as previously defined. The terms "hydroxyalkyl", "deuteroalkyl" and "fluoroalkyl" refer to an alkyl radical substituted by one or more hydroxy, deuterium or fluoro groups respectively.

Specific embodiments of the reactions of the new process are presented in the following Examples. Process Schemes I, II, III and IV depict the structures of the compounds described in these Examples, such that products identified by Arabic numerals (e.g. 1, 2, 3, 3a, etc.) correspond to the structures so numbered in the Process Schemes.

EXAMPLES

Experimental

General: Unless otherwise noted, all air-sensitive reactions were run under Ar atmosphere, and reagents were added through septa using syringes. Tetrahydrofuran and diethyl ether were distilled from Na benzophenone ketyl prior to use. Pyridine, triethylamine, diisopropylamine, acetonitrile, methyl sulfoxide and methylene chloride were distilled from calcium hydride. Toluene and MeOH were distilled from Na. N,N-Dimethylformamide was distilled from 4A molecular sieves. Ethyl acetate and 1,4-dioxane were reagent grade. All chemicals were used as received. Column chromatography was performed on silica gel (Wako Pure Chem. Ind. Ltd. Wakogel C-200, ~200 mesh). NMR spectra were recorded in $CDCl_3$ on a Bruker ARX-400 MHz spectrometer. Chemical shifts are reported in parts per million (ppm, δ) downfield from tetramethylsilane. Mass spectra were recorded on a JEOL JMS-AX505HA spectrometer run at 70 eV for electronic ionization (EI).

Example 1

(See Scheme I)
Synthesis of 2-deoxy-glucose Derivative 7 from D-glucose [Method A]

[Step 1]: (D)-Glucose ⟶ Compound 4

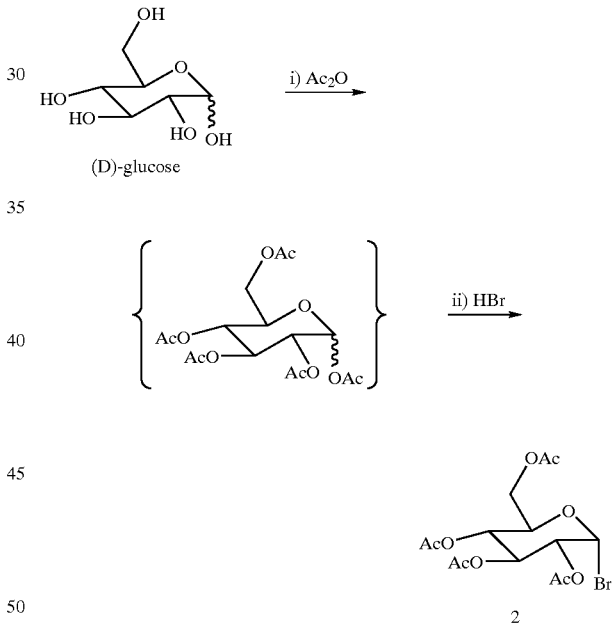

To a stirred suspension of D-glucose (1 g) in acetic anhydride (200 ml) was added 70% perchloric acid (1.2 mL). Additional D-glucose (49 g, total 50 g, 0.28 mol) was added in small portions over a period of 1.5 h. The reaction mixture was maintained below 40° C. by occasional cooling in an ice-water bath. After addition was complete, the solution was cooled to 20° C., and hydrogen bromide (33 wt. % solution in acetic acid, 200 mL) was added over a period of 30 min. After being stirred for 3 h, the reaction mixture was diluted with methylene chloride ($CH_2claim_2$, 700 mL), and washed successively with ice-water and cold 5% sodium hydrogencarbonate ($NaHCO_3$), and then dried over magnesium sulfate ($MgSO_4$). The solvent was removed by reduced pressure to afford 2 (123 g) as a syrup. This product was used directly in the following reaction.

2: $^1$H NMR (CDCl$_3$) δ: 2.04, 2.06, 2.10 and 2.11 (each 3H, s, COCH$_3$), 4.13 (1H, d, J=10.7 Hz, 6-H), 4.28~4.35 (2H, m, 5, 6-H), 4.85 (1H, dd, J=9.7, 4.0 Hz, 2-H) 5.17 (1H, t, J=9.7 Hz, 3 or 4-H), 5.56 (1H, t, J=9.7 Hz, 3 or 4-H), 6.62 (1H, d, J=4.0 Hz, 1-H).

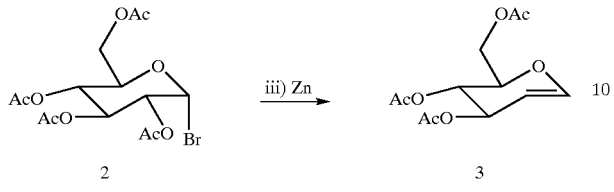

The crude bromide 2 (56.1 g, 0.14 mol) was added slowly to a slurry of zinc dust (60 g, 0.92 mol) in 50% aqueous acetic acid (500 mL) over a period of 1 h with mechanical stirring while maintaining the temperature at −15~−20° C. in dry ice-acetonitrile (CH$_3$CN) bath. After addition was complete, the reaction mixture was stirred for an additional 1 h at 0° C., and then the reaction mixture was filtered by suction. The filtrate was diluted with methylene chloride (800 mL) and extracted with ice-water (3×250 mL). The organic layer was washed with cold saturated NaHCO$_3$ (2×200 mL) and brine, and dried over MgSO$_4$. The solvent was evaporated in vacuo to give 3 (37.5 g) as a syrup. This product was used directly in the next step.

3: $^1$H NMR (CDCl$_3$) δ: 2.05, 2.13 and 2.15 (each 3H, s, COCH$_3$), 4.20 (1H, dd, J=12.0, 3.1 Hz, 6-H), 4.26 (1H, m, 5-H), 4.40 (1H, dd, J=12.0, 5.7 Hz, 6-H), 4.85 (1H, dd, J=6.2, 3.2 Hz, 2-H), 5.23 (1H, dd, J=7.5, 5.7 Hz, 4-H), 5.34 (1H, m, 3-H), 6.47 (1H, d, J=6.2 Hz, 1-H).

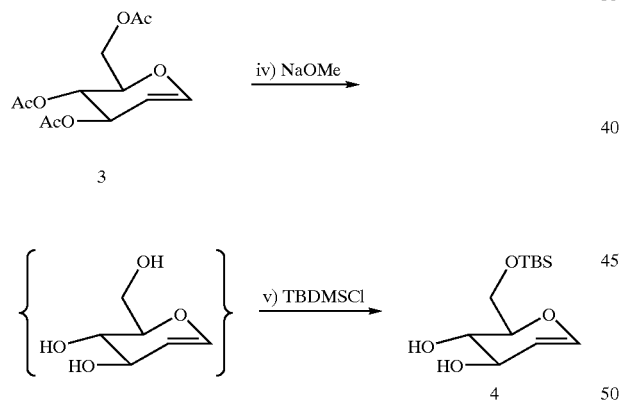

To a solution of the crude acetyl glucal 3 (12.5 g, 45.9 mmol) in dry MeOH (150 mL) was added a solution of sodium methoxide (NaOMe, 4.59 mmol) in dry MeOH (1 mL) at room temperature. The reaction mixture was stirred for 30 min and evaporated to dryness. The residue was dissolved in dry N,N-dimethylformamide (DMF, 150 mL) at 0° C. and to this solution was added imidazole (9.4 g, 137.7 mmol) and tert-butyldimethylsilyl chloride (10.4 g, 68.9 mmol). The reaction mixture was stirred for 3 h at room temperature, diluted with icewater, and extracted with 50% ethyl acetate (AcOEt)-hexane. The organic extract was washed with brine, dried over MgSO$_4$, and evaporated in vacuo. The residue was purified by chromatography on silica gel (200 g) using 50% AcOEt-hexane to yield 4 (7.15 g, 65% from D-glucose).

4: $^1$H NMR (CDCl$_3$) δ: 0.11 (6H, s, Si—CH$_3$), 0.91 (9H, s, Si-tBu), 3.79 (2H, m 6-H), 3.92 and 3.99 (each 1H, m, 4, 5-H), 4.26 (1H, m, 3-H), 4.72 (1H, dd, J=6.1, 2.0 Hz, 2H), 6.31 (1H, dd, J=6.0, 2.0 Hz, 1-H).

Mass m/z (%): 260 (no M$^+$), 224 (1), 203 (20), 185 (85), 167 (14), 75 (100).

[Step 2]: Compound 4 ⟶ Compound 5

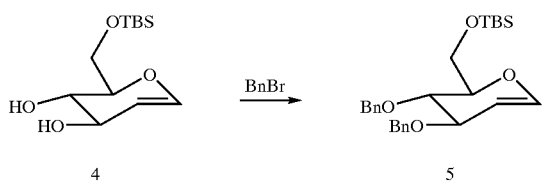

To a stirred, cold (0° C.) solution of 4 (4.42 g, 17.0 mmol) dissolved in dry DMF (50 mL) and dry tetrahydrofuran (THF, 5 mL) was added sodium hydride (60% dispersion in oil, 2.72 g, 68.0 mmol) and benzyl bromide (8.72 g, 51.0 mmol). Stirring was continued for 40 min at 0° C., and the reaction mixture was quenched with water. After extraction with 50% AcOEt-hexane, the combined organic extract was washed with brine, dried over MgSO$_4$, and evaporated to dryness. The residue was purified by chromatography on silica gel (150 g) using 3% AcOEt-hexane to afford 5 (7.22 g, 97%).

5: $^1$H NMR (CDCl$_3$) δ: 0.06 and 0.07 (each 3H, s, Si—CH$_3$), 3.87~3.98 (4H, m, 4, 5, 6-H), 4.20 (1H, m, 3-H), 4.58 and 4.64 (each 1H, d, J=11.7 Hz, CH$_2$Ph), 4.74 and 4.86 (each 1H, d, J=11.2 Hz, CH$_2$Ph), 4.83 (1H, dd, J=6.1, 2.5 Hz, 2-H), 6.38 (1H, dd, J=6.2, 1.2 Hz, 1-H), 7.28-7.35 (10H, m, arom H).

Mass m/z (%): 440 (no M$^+$), 383 (4), 332 (2), 277 (10), 253 (5), 221 (100).

[Step 3]: Compound 5 ⟶ Compound 6

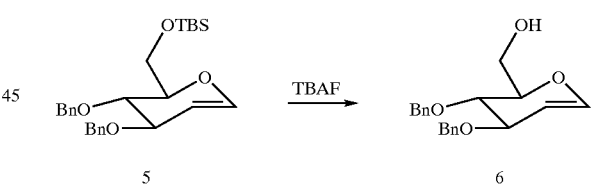

To a stirred solution of 5 (14.5 g. 32.9 mmol) in dry THF (50 mL) was added tetrabutylammonium fluoride (Bu$_4$NF, 1.0 M solution in THF, 65.8 mmol) at 0° C. and stirring was continued for 2.5 h. The reaction mixture was quenched with ice-water and extracted with AcOEt. The organic extract was washed with brine, dried over MgSO$_4$, and evaporated in vacuo. The residue was purified by chromatography on silica gel (200 g) with 25% AcOEt-hexane to give 6 (9.42 g, 88%).

6: $^1$H NMR (CDCl$_3$) δ: 3.80 (1H, dd, J=8.6, 6.2 Hz, 4-H), 3.85 (2H, d, J=4.1 Hz, 6-H), 3.93 (1H, dd, J=8.6, 4.1 Hz, 5-H), 4.23 (1H, ddd, J=6.2, 2.7, 1.1 Hz, 3-H), 4.56 and 4.66 (each 1H, d, J=11.6 Hz, CH$_2$Ph), 4.72 and 4.86 (each 1H, d, J=11.4 Hz, CH$_2$Ph), 4.88 (1H, dd, J=6.1, 2.7 Hz, 2-H), 6.39 (1H, dd, J=6.1, 1.1 Hz, 1-H), 7.28~7.35 (10H, m, arom H).

Mass m/z (%): 326 (M$^+$, 0.2), 308 (0.1), 295 (0.1), 235 (3), 218 (12), 189 (9), 163 (70), 91 (100).

[Step 4]: Compound 6 ⟶ Compound 7a, 7b

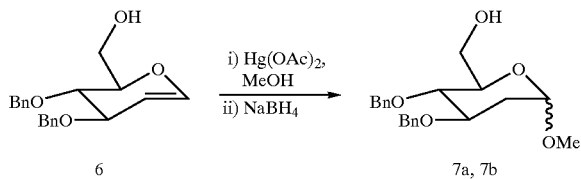

To a stirred solution of 6 (9.41 g, 28.8 mmol) in dry MeOH (150 mL) was added portionwise mercury(II) acetate [(CH$_3$CO$_2$)$_2$Hg, 11.00 g, 34.5 mmol] over a 30 min period. After being stirred for 1.5 h at room temperature, the mixture was cooled to 0° C. To this solution was portionwise added over a period of 1 h sodium borohydride (NaBH$_4$, 1.31 g, 34.5 mmol) and the reaction mixture was stirred for 4 h. The mixture was filtered and the filtrate was concentrated to a small volume. Water and chloroform (CHCl$_3$) were added, the organic phase was separated, and the aqueous phase was reextracted with CHCl$_3$. The organic extract was washed with water, dried over MgSO$_4$, and evaporated to dryness. The residue was subjected to chromatography on silica gel (150 g) using 30% AcOEt-hexane to yield 7 (α-anomer: 6.92 g, 67%; β-anomer: 1.86 g, 18%) as a mixture of anomeric isomers. 7a was isolated as a single isomer, while 7b was obtained as a mixture of 7a and 7b.

7a (α-anomer): $^1$H NMR (CDCl$_3$) δ: 1.65 and 2.29 (each 1H, m, 2-H), 3.30 (3H, s, OCH$_3$), 3.50 (1H, t, J=9.4 Hz, 4-H), 3.64 (1H, dm, J=9.4 Hz, 5-H), 3.75 (1H, dd, J=11.7, 4.1 Hz, 6-H), 3.81 (1H, dd, J=11.7, 3.0 Hz, 6-H), 3.99 (1H, ddd, J=11.5, 9.4, 5.0 Hz, 3H), 4.63 and 4.67 (each 1H, d, J=11.6 Hz, CH$_2$Ph), 4.68 and 4.95 (each 1H, d, J=11.1 Hz, CH$_2$Ph), 4.80 (1H, br. d, J=2.9 Hz, 1-H), 7.26~7.36 (10H, m, arom H).

7b (β-anomer): $^1$H NMR (CDCl$_3$) δ: 1.56 and 2.34 (each 1H, m, 2-H), 3.31 (1H, m), 3.49 (3H, s, OCH$_3$), 4.40 (1H, dd, J=9.8, 2.0 Hz, 1-H).

7a and 7b: Mass m/z (%): 358 (M$^+$, 0.7), 327 (1.5), 326 (1), 267 (87), 235 (23), 91 (100).

Example 2
(See Scheme II):
Synthesis of 2-deoxy-glucose Derivative 7 from D-glucose [Method B]

[Step 1]: Compound 3 ⟶ Compound 8a, 8b

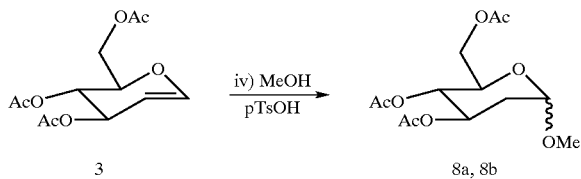

To a solution of the crude triacetyl glucal 3 (9.54 g, 35.0 mmol) in CH$_3$CN (150 mL) was successively added LiBr (3.65 g, 42.0 mmol), MeOH (2.25 g, 70.2 mmol), and p-toluenesulfonic acid monohydrate (p-TsOH.H$_2$O, 954 mg) at room temperature. After being stirred for 3 h, the reaction mixture was concentrated to a small volume, diluted with cold 5% NaHCO$_3$ solution, and extracted with CHCl$_3$. The organic extract was washed with ice-water, dried over MgSO$_4$, and evaporated in vacuo. The residue was chromatographed on silica gel (150 g) using 30% AcOEt-hexane to give 8 (9.01 g, 92% from D-glucose) (α-anomer:β-anomer=ca. 10:1). 8a was isolated as a single isomer, while 8b was obtained as a mixture of 8a and 8b.

8a (α-anomer): $^1$H NMR (CDCl$_3$) δ: 1.81 (1H, m, 2-H), 2.01, 2.04 and 2.10 (each 3H, s, COCH$_3$), 2.25 (1H, m, 2-H), 3.35 (3H, s, OCH$_3$), 3.95 (1H, ddd, J=9.7, 4.7, 2.3 Hz, 5-H), 4.08 (1H, dd, J=12.3, 2.3 Hz, 6-H), 4.31 (1H, dd, J=12.2, 4.7 Hz, 6-H), 4.84 (1H, d, J=3.1 Hz, 1-H), 5.00 (1H, t, J=9.7 Hz, 4-H), 5.30 (1H, ddd, J=11.5, 9, 7, 5.3 Hz, 3-H).

Mass m/z (%): 304 (M$^+$, 0.1), 273 (2), 231 (4), 213 (25), 184 (9), 171 (15), 111 (33), 100 (100).

8b (β-anomer): $^1$H NMR (CDCl$_3$) δ: 1.73 (1H, m, 2-H), 2.03, 2.04 and 2.09 (each 3H, s, COCH$_3$), 2.32 (1H, m, 2-H), 3.51 (3H, s, OCH$_3$), 3.62 (1H, m, 5-H), 4.12 (1H, dd, J=12.2, 2.4 Hz, 6-H), 4.31 (1H, dd, J=12.2, 4.8 Hz, 6-H), 4.48 (1H, dd, J=9.6, 2.0 Hz, 1-H), 5.00 (2H, m, 3, 4-H).

[Step 2]: Compound 8a ⟶ Compound 9a

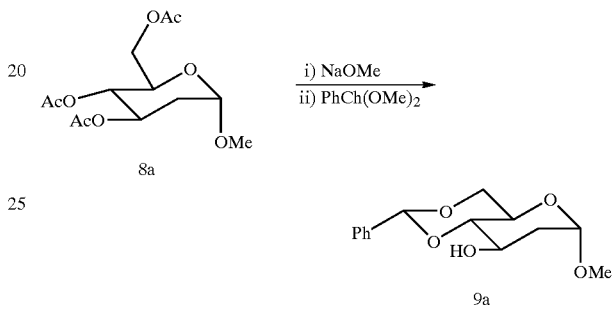

To a solution of 8a (α-anomer, 10.27 g, 33.8 mmol) in dry MeOH (150 mL) was added a solution of NaOMe (3.38 mmol) in dry MeOH (1 mL) at room temperature. The reaction mixture was stirred for 30 min and evaporated to dryness. The residue was dissolved in dry CH$_3$CN (150 mL) and to this solution was added benzaldehyde dimethyl acetal (7.70 g, 51.3 mmol) and p-TsOH.H$_2$O (1.03 g). The reaction mixture was stirred for 24 h at room temperature, concentrated to a small volume, and cold 5% NaHCO$_3$ and AcOEt were added. The organic phase was separated and the aqueous phase was reextracted with AcOEt. The combined organic extract was washed with brine, dried over MgSO$_4$, and evaporated in vacuo. The residue was purified by chromatography on silica gel (200 g) using 30% AcOEt-hexane to yield 9a (6.55 g, 73%).

9a (α-anomer): $^1$HNMR (CDCl$_3$) δ: 1.80 (1H, m, 2-H), 2.24 (1H, m, 2-H), 3.36 (3H, s, OCH$_3$), 3.49 (1H, t, J=9.0 Hz, 5-H), 3.76 (1H, t, J=9.5 Hz, 6-H), 380 (1H, m), 4.20 (1H, m), 4.27 (1H, m), 4.82 (1H, d, J=3.4 Hz, 1-H), 5.58 (1H, s, CHPh), 7.35-7.52 (5H, m, arom H).

Mass m/z (%): 266 (M$^+$, 53), 234 (8), 179 (100), 105 (65).

[Step 3]: Compound 9a ⟶ Compound 10a

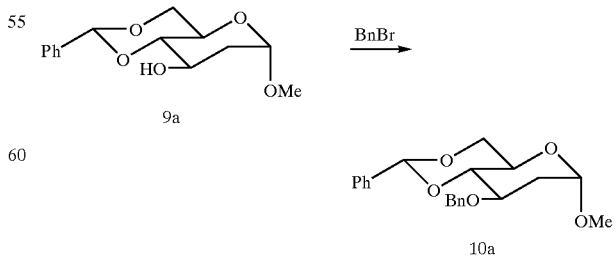

To a solution of 9a (8.69 g, 32.7 mmol) in dry DMF-dry THF (150 mL-15 mL) was added sodium hydride (60% dispersion in oil, 2.62 g, 65.4 mmol) at 0° C. and the mixture was stirred for 5 min. To this solution was added benzyl bromide (8.35 g, 49.1 mmol) and the mixture was stirred for 1.5 h at 0° C. followed by stirring for 2 h at room temperature. The reaction mixture was poured into ice-water and extracted with 50% AcOEt-hexane. The organic layer was washed with brine, dried over MgSO$_4$, and evaporated in vacuo. The residue was purified by chromatography on silica gel (150 g) with 10% AcOEt-hexane to afford 10a (10.47 g, 90%).

L0a (α-anomer): $^1$H NMR (CDCl$_3$) δ: 1.80 (1H, m, 2-H), 2.26 (1H, m, 2-H), 3.33 (3H, s, OCH$_3$), 3.69 (1H, t, J=6.5 Hz), 3.79 (2H, m), 4.01 (1H, m), 4.26 (1H, m), 4.68 and 4.83 (each 1H, d, J=11.9 Hz, CH$_2$Ph), 4.80 (1H, d, J=3.2 Hz, 1-H), 5.62 (1H, s, CHPh), 7.20~7.50 (5H, m, arom H).

Mass m/z (%): 356 (M$^+$, 43), 324 (6), 219 (10), 91 (100).

[Step 4]: Compound 10a ⟶ Compound 7a

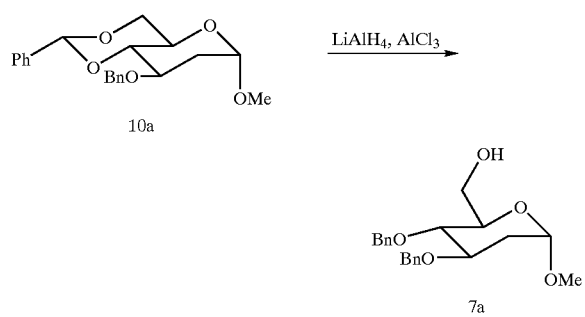

To a suspension of lithium aluminum hydride (LiAlH$_4$, 0.19 g, 5.05 mmol) in dry diethyl ether (10 mL) and dry CH$_2$Cl$_2$ (10 mL) was slowly added a solution of 10a (1.8 g, 5.05 mmol) in dry diethyl ether (10 mL) and dry CH$_2$claim$_2$ (10 mL) at room temperature. To this suspension was portionwise added aluminum chloride (0.67 g, 5.05 mmol) and the mixture was stirred for 1 h. Excess LiAlH$_4$ was destroyed by addition of wet ether and filtered. The filtrate was diluted with ice-water and extracted with AcOEt. The organic extract was washed successively with cold 5% NaHCO$_3$ and brine, and dried over MgSO$_4$. Evaporation of the solvent gave colorless syrup, which was purified by chromatography on silica gel (75 g) using 30% AcOEt-hexane to give 7a (1.52 g, 84%).

Example 3

(See Scheme III):

In the following synthesis of the cyclohexanone derivative 19 from 2-deoxy-glucopyranosides 7, we separated most of the synthetic intermediates 11~18 which exist as two anomeric isomers or two isomers at C(1) position. In a practical synthesis, it is unnecessary to separate those isomers in each reaction step.

[Step 5]: Compound 7a, 7b ⟶ Compound 11a, 11b

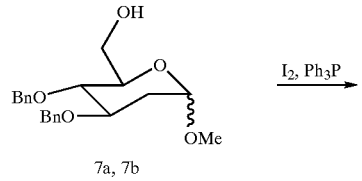

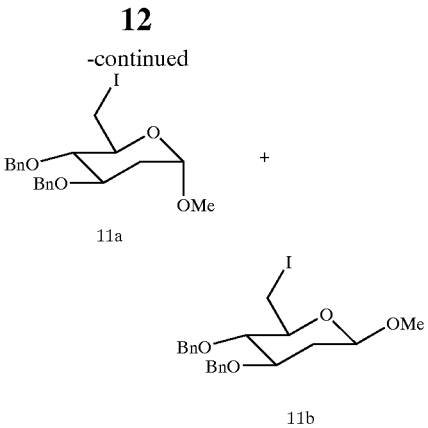

A mixture of the two anomeric isomers 7a, 7b (6.40 g, 17.9 mmol), triphenylphosphine (Ph$_3$P, 5.64 g, 21.5 mmol), imidazole (3.51 g, 51.6 mmol), iodine (12, 4.99 g, 19.6 mmol, freshly sublimated) in dry THF (70 mL) was stirred for 5 h at 0° C. and overnight at room temperature. After being stirred for 6 h, additional Ph$_3$P, imidazole, and 12 (each 0.5 equivalent) were added to the reaction mixture. The reaction mixture was diluted with AcOEt, washed successively cold 5% NaHCO$_3$, 2N sodium thiosulfate (Na$_2$S$_2$O$_3$), and brine. The organic extract was dried over MgSO$_4$ and evaporated in vacuo. The residue was purified by chromatography on silica gel (150 g) using 2% AcOEt-hexane to afford 11a (α-anomer: 5.52 g, 66%) and 11b (β-anomer: 1.34 g, 16%).

11a (α-anomer): $^1$H NMR (CDCl$_3$) δ: 1.69 and 2.30 (each 1H, m, 2-H), 3.31~3.45 (3H, m, 4, 5, 6-H), 3.36 (3H, s, OCH$_3$), 3.54 (1H, dd, J=9.6, 1.8 Hz, 6-H), 4.00 (1H, ddd, J=11.4, 8.5, 5.1 Hz, 3-H), 4.60 and 4.66 (each 1H, d, J=11.5 Hz, CH$_2$Ph), 4.72 and 5.00 (each 1H, d, J=11.0 Hz, CH$_2$Ph), 4.83 (1H, br. D, J=2.8 Hz, 1-H), 7.27~7.37 (10H, m, arom H).

Mass m/z (%): 468 (M$^+$, 1), 437 (7), 377 (40), 345 (3), 271 (28), 253 (6), 239 (8), 91 (100).

11a (β-anomer): $^1$H NMR (CDCl$_3$) δ: 1.61 and 2.35 (each 1H, m, 2-H), 3.14 (1H, ddd, J=8.7, 7.3, 2.5 Hz, 5-H), 3.29 (1H, dd, J=10.4, 7.4 Hz, 6-H), 3.32 (1H, t, J=8.8 Hz, 4-H), 3.52 (3H, s, OCH$_3$), 3.54 (1H, dd, J=10.4, 2.5 Hz, 6-H), 3.68 (1H, ddd, J=11.5, 8.5, 5.0 Hz, 3-H), 4.39 (1H, dd, J=9.7, 1.9 Hz, 1-H), 4.59 and 4.68 (each 1H, d, J=11.6 Hz, CH$_2$Ph), 4.70 and 5.99 (each 1H, d, J=10.9 Hz, CH$_2$Ph), 7.28~7.37 (10H, m, arom H).

Mass m/z (%): 469 (M$^+$, 0.2), 436 (3), 377 (13), 345 (7), 271 (29), 253 (4), 239 (9), 91 (100).

[Step 6a]: Compound 11a ⟶ Compound 12a

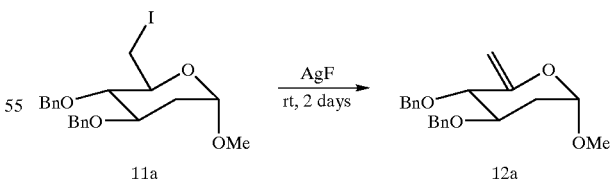

Powdered silver fluoride (AgF, 2.1 g, 16.5 mmol) was added to a solution of 11a (2.0 g, 4.27 mmol) in dry pyridine (35 mL). After being stirred in the dark for 2 days, the reaction mixture was filtered and the filtrate was partitioned between AcOEt and ice-water. After phase separation, the aqueous layer was reextracted with AcOEt. The combined organic extract was washed with water and brine, dried over MgSO$_4$, and evaporated to dryness. The residue was purified by chromatography on silica gel (30 g) with 3% AcOEt-hexane to give 12a (1.35 g, 93%).

12a (α-anomer): $^1$H NMR (CDCl$_3$) δ: 1.87 and 2.27 (each 1H, m, 2-H), 3.41 (3H, s, OCH$_3$), 3.90 (2H, m, 3, 4-H), 4.63 and 4.71 (each 1H, d, J=11.7 Hz, CH$_2$Ph), 4.73 and 4.78 (each 1H, d, J=11.7 Hz, CH$_2$Ph), 4.74 and 4.81 (each 1H, br. S, 6-H), 4.86 (1H, t, J=3.2 Hz, 1-H), 7.28~7.38 (10H, m, arom H).

[Step 6b]: Compound 11b ⟶ Compound 12b

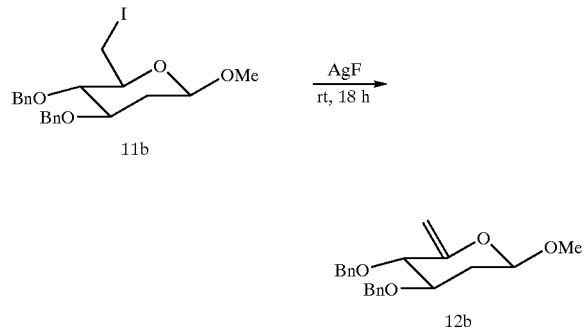

To a stirred solution of 11b (895 mg, 1.91 mmol) in dry pyridine (15 mL) was added powdered AgF (486 mg, 3.82 mmol) and the reaction mixture was stirred in the dark for 18 h at room temperature. Work-up similar to that described above afforded 12b (618 mg, 95%).

12b (β-anomer): $^1$HNMR(CDCl$_3$) δ: 1.86 (1H, m, 2-H), 2.28 (1H, ddd, J=14.0, 5.7, 3.4 Hz, 2-H), 3.50 (3H, s, OCH$_3$), 3.67 (1H, dt, J=7.0, 5.7 Hz, 3-H), 3.96 (1H, d, J=5.7 Hz, 4-H), 4.58 and 4.73 (each 1H, d, J=11.6 Hz, CH$_2$Ph), 4.63 (1H, s, 6-H), 4.64 (2H, s, CH$_2$Ph), 4.73 (1H, dd, J=5.9, 3.4 Hz, 1-H), 4.78 (1H, s, 6-H), 7.27~7.35 (10H, m, arom H).

[Step 7a]: Compound 12a ⟶ Compound 13a, b

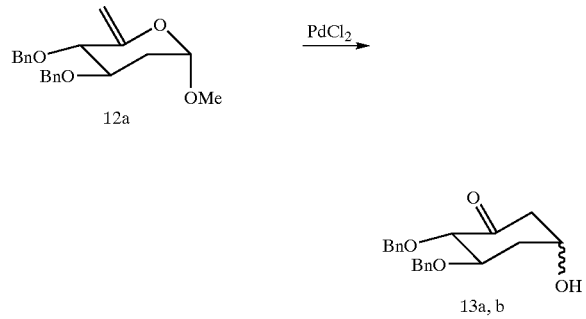

To a stirred solution of 12a (1.07 g, 3.14 mmol) in 1,4-dioxane-water (15 mL, 2:1; v/v) was added palladium (II) chloride (PdCl$_2$, 113 mg, 0.64 mmol) and the reaction mixture was heated at 60° C. for 1.5 h. AcOEt and water were added to the mixture and the organic phase was separated. The aqueous phase was reextracted with AcOEt and the combined organic extract was washed with water and brine, and then dried over MgSO$_4$. Removal of the solvent gave the residue, which was purified by chromatography on silica gel (30 g) using 50% AcOEt-hexane to yield 13 (939 mg, 92%) in a mixture of 1α-OH (13a): 1β-OH (13b)=ca.6:1 ratio.

[Step 7b]: Compound 12b ⟶ Compound 13a, b

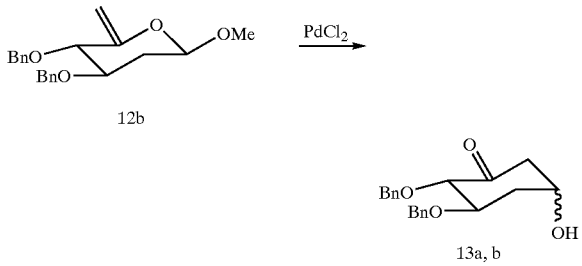

A mixture of 12b (1.34 g, 3.94 mmol) and PdCl$_2$ (140 mg, 0.79 mmol) in 1,4-dioxanewater (21 mL, 2:1) was heated at 60° C. for 1.5 h. Work-up similar to that described above gave 13 (1.17 g, 91%) in a mixture of 1α-OH (13a): 1β-OH (13b)=ca. 6:1 ratio.

13a (1-αOH): $^1$H NMR (CDCl$_3$) δ: 2.03 and 2.32 (each 1H, m, 2-H), 2.64 (2H m, 6-H), 3.98 (1H, d, J=7.5 Hz, 4-H), 4.04 (1H, ddd, J=8.0, 7.5, 4.1 Hz, 3-H), 4.36 (1H, m, 1-H), 4.55, 4.61, 4.75 and 4.82 (each 1H, d, J=11.7 Hz, CH$_2$Ph) 7.28~7.39 (10H, m, arom H).

13b (1-βOH): $^1$H NMR (CDCl$_3$) δ: 4.22 (1H, m, 1-H), 4.47, 4.54, 4.64 and 4.79 (each 1H, d, J=11.7 Hz, CH$_2$Ph).

13a and 13b: Mass m/z (%): 326 (M$^+$, 2), 308 (5), 278 (2), 235 (3), 217 (2), 91 (100).

[Step 8]: Compound 13a, b ⟶ Compound 14a, b

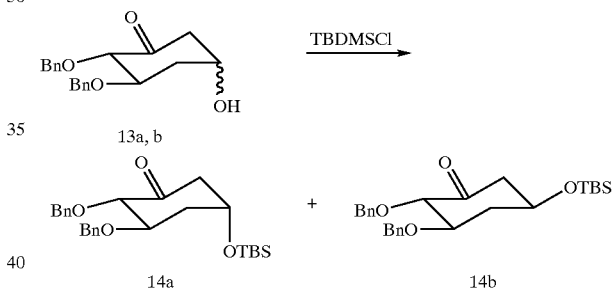

A mixture of 13a,b (1.95 g, 5.97 mmol), imidazole (813 mg, 11.9 mmol), tertbutyldimethylsilyl chloride (1.35 g, 8.96 mmol) in dry DMF (20 mL) was stirred at for 1 h 0° C. followed by for 1.5 h at room temperature. Additional imidazole (203 mg, 2.89 mmol) and tert butyldimethylsilyl chloride (225 mg, 1.49 mmol) were added and stirring was continued for 2.5 h. The reaction mixture was poured into ice-water and extracted with 50% AcOEt-hexane. The organic extract was washed with brine, dried over MgSO$_4$, and evaporated in vacuo. The residue was purified by chromatography on silica gel (30 g) using 5% AcOEt-hexane to afford 14 (2.54 g, 97%) in approximately 1α-OH:1β-OH=6.5:1 ratio. The two isomers were separated by rechromatography on silica gel to give 1α-OTBS 14a and 1β-OTBS 14b.

14a (1-αOTBS): $^1$H NMR (CDCl$_3$) δ: −0.02 and 0.02 (each 3H, s, Si—CH$_3$), 0.81 (9H, s, Si-tBu), 1.87 and 2.19 (each 1H, m, 2-H), 2.50 (2H, m, 6-H), 4.01 (2H, m, 3, 4-H), 4.27 (1H, m, 1-H), 4.57, 4.63, 4.78 and 4.87 (each 1H, d, J=11.8 Hz, CH$_2$Ph), 7.27~7.42 (10H, m, arom H).

Mass m/z (%): 440 (M$^+$, 3), 383 (2), 349 (3), 333 (5), 308 (7), 277 (6), 275 (4), 243 (3), 91 (100).

14b (1-βOTBS): $^1$H NMR (CDCl$_3$) δ: 0.036 and 0.044 (each 3H, s, Si—CH$_3$), 0.86 (9H, s, Si-tBu), 1.90 (1H, dt, J=12.0, 11.0 Hz, 6-H), 2.35 (1H, m, 2-H), 2.48 (1H, t, J=12.0

Hz, 6-H), 2.64 (1H, ddd, J=13.1, 4.7, 2.4 Hz, 2-H), 3.54 (1H, ddd, J=11.4, 9.4, 4.7 Hz, 3-H), 3.77 (1H, tt, J=11.0, 4.5 Hz, 1-H), 4.08 (1H, d, J=9.3 Hz, 4-H), 4.57, 4.65, 4.80 and 4.90 (each 1H, d, J=11.6 Hz, CH$_2$Ph), 7.28-7.41 (10H, m, arom H).

Mass m/z (%): 440 (M$^+$, 4), 383 (2), 349 (3), 333 (3), 308 (15), 277 (15), 275 (4), 243 (12), 91 (100).

[Step 9a]: Compound 14a ⟶ Compound 15a

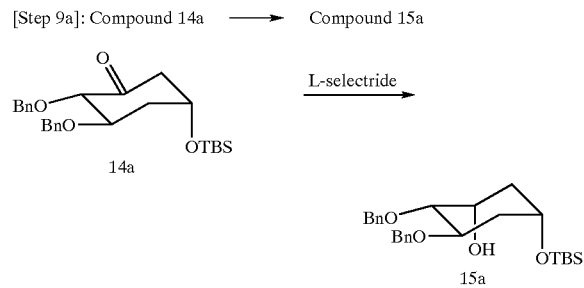

To a stirred solution of 14a (923 mg, 2.09 mmol) in dry THF (10 mL) was dropwise added L-Selectride (lithium tri-sec-butylborohydride, 1.0 M solution in THF, 3.14 mmol) at −78° C., and the reaction mixture was stirred for 1.5 h at the same temperature. The mixture was quenched with ice-water and extracted with AcOEt. The organic extract was washed with brine, and dried over MgSO$_4$. Removal of the solvent gave the residue, which was chromatographed on silica gel (20 g) using 10% AcOEt-hexane to give 15a (866 mg, 94%) as a sole product. No trace of epimeric alcohol was detected.

15a (1-αOTBS): $^1$H NMR (CDCl$_3$) δ: 0.04 and 0.06 (each 3H, s, Si—CH$_3$), 0.86 (9H, s, Si-tBu), 1.70 and 1.90 (each 2H, m, 2, 6-H), 3.47 (1H, dd, J=6.9, 3.1 Hz, 4-H), 3.98, 4.05 and 4.10 (each 1H, m, 1, 3, 5-H), 4.63 and 4.70 (each 1H, d, J=11.8 Hz, CH$_2$Ph), 4.67 and 4.69 (each 1H, d, J=10.4 Hz, CH$_2$Ph), 7.28~7.40 (10H, m, arom H).

Mass m/z (%): 442 (M$^+$, 0.2), 399 (2), 351 (4), 333 (0.2), 293 (2), 277 (2), 91 (100).

[Step 9b]: Compound 14b ⟶ Compound 15b

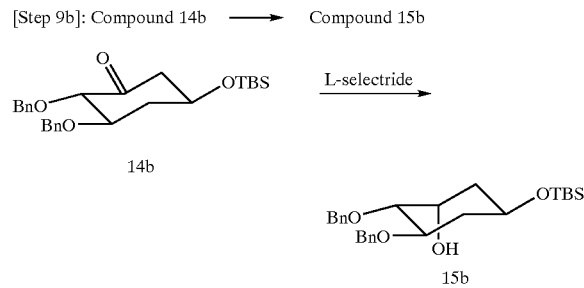

To a cold (−78° C.) solution of 14b (140 mg, 0.32 mmol) in dry THF (1 mL) was added L-Selectride (1.0 M solution in THF, 0.48 mmol) and the mixture was stirred for 1.5 h. Work-up similar to that described above afforded 15b (107 mg, 76%) as a single isomer together with the recovered starting material 14b (11%).

15b (1-βOTBS): $^1$H NMR (CDCl$_3$) δ: 0.05 (6H, 5, Si—CH$_3$), 0.87 (9H, s, Si-tBu), 1.37 (2H, m), 2.13 and 2.22 (each 1H, m), 3.40 (1H, dd, J=9.0, 3.1 Hz, 4-H), 3.75 (1H, ddd, J=11.7, 9.1, 4.6 Hz, 3 or 5-H), 4.03 (1H, tt, J=11.0, 4.3 Hz, 1-H), 4.12 (1H, dd, J=6.1, 3.1 Hz, 3 or 5-H), 4.66 and 4.69 (each 1H, d, J=11.6 Hz, CH$_2$Ph), 4.68 and 4.78 (each 1H, d, J=11.6 Hz, CH$_2$Ph), 7.27~7.37 (10H, m, arom H).

[Step 10a]: Compound 15a ⟶ Compound 16a

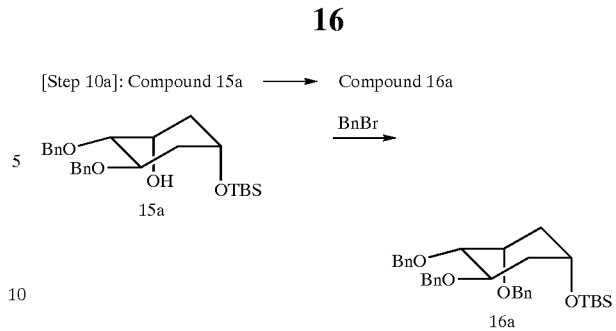

A mixture of 15a (904 mg, 2.04 mmol), sodium hydride (NaH, 60% dispersion in oil, 164 mg, 4.08 mmol) and benzyl bromide (523 mg, 3.06 mmol) in dry DMF-dry THF (11 mL, 10:1) was stirred for 4 h at 0° C. The reaction mixture was diluted with ice-water and extracted with 50% AcOEt-hexane. The organic extract was washed with brine, dried over MgSO$_4$, and evaporated in vacuo. The residue was purified by chromatography on silica gel (30 g) with 5% AcOEt-hexane to afford 16a (1.02 g, 94%).

16a (1-αOTBS): $^1$H NMR (CDCl$_3$) δ: 0.05 and 0.06 (each 3H, s, Si—CH$_3$), 0.88 (9H, s, Si-tBu), 1.71 (1H, m), 1.92 (2H, m), 2.02 (1H, m), 3.69-3.76 (3H, m, 3, 4, 5-H), 3.90 (1H, tt, J=11.0, 4.5 Hz, 1-H), 4.37, 4.48, 4.50, 4.55, 4.57 and 4.76 (each 1H, d, J=12.1 Hz, CH$_2$Ph), 7.26~7.38 (15H, m, arom H).

Mass m/z (%): 532 (M$^+$, 0.3), 441 (11), 383 (1), 335 (1), 317 (1), 277 (4), 247 (5), 91 (100).

[Step 10b]: Compound 15b ⟶ Compound 16b

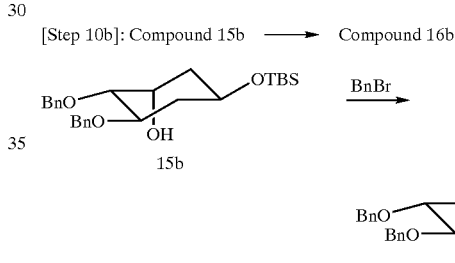

A mixture of 15b (128 mg, 0.29 mmol), sodium hydride (60% dispersion in oil, 23 mg, 0.58 mmol) and benzyl bromide (74 mg, 0.43 mmol) in dry DMF-dry THF (1.65 mL, 10:1) was stirred at 0° C. for 2 h. Work-up similar to that described above afforded 16b (141 mg, 92%).

16b (1-βOTBS): $^1$H NMR (CDCl$_3$) δ: 0.04 and 0.05 (each 3H, s, Si—CH$_3$), 0.87 (9H, s, Si-tBu), 1.28 (1H, m), 1.42 (1H, dt, J=12.1, 11.1 Hz), 2.11 and 2.25 (each 1H, m), 3.39 (1H, dd, J=9.2, 2.9 Hz, 4-H), 3.90 (2H, m, 3, 5-H), 4.03 (1H, tt, J=10.8, 4.5 Hz, 1-H), 4.61-4.77 (6H, m, CH$_2$Ph), 7.27~7.37 (15H, m, arom H).

[Step 11a]: Compound 16a ⟶ Compound 17a

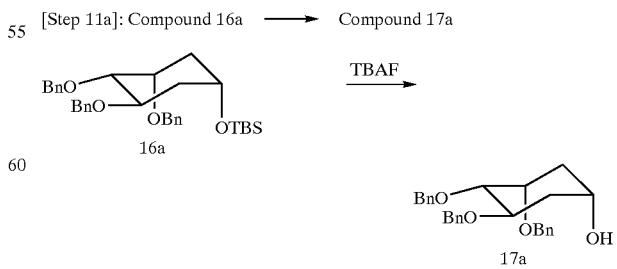

A mixture of 16a (1.06 g, 1.99 mmol) and Bu$_4$NF (1.0 M solution in THF, 3.0 mmol) in dry THF (10 mL) was stirred for 30 min at 0° C. followed by at room temperature. After 5 h stirring, additional Bu₄NF (3.0 mmol) was added and the reaction mixture was further stirred for 20 h at room temperature. The mixture was diluted with ice-water and AcOEt and the organic phase was separated. The aqueous layer was reextracted with AcOEt and the combined organic extract was washed with brine, dried over $MgSO_4$, and evaporated to dryness. The residue was purified by chromatography on silica gel (35 g) with 40% AcOEt-hexane to yield 17a (797 mg, 95%).

17a (1-αOH): ¹H NMR (CDCl₃) δ: 1.69-1.80 (2H, m), 2.03~2.10 (2H, m), 3.58(1H, dd, J=6.8, 2.2 Hz, 4-H), 3.94~4.13 (3H, m, 1, 3, 5-H), 4.61 (2H, s, CH₂Ph), 4.63~4.70 (each 1H, d, J=12.1 Hz, CH₂Ph), 4.72 (2H, s, CH₂Ph), 7.27~7.34 (15H, m, arom H).

Mass m/z (%): 418 (M⁺, 0.1), 327 (25), 309 (1), 91 (100).

[Step 11b]: Compound 16b ⟶ Compound 17b

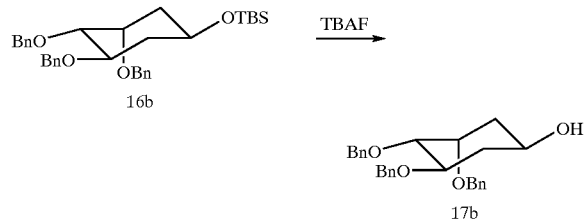

A mixture of 16b (140 mg, 0.26 mmol) and Bu₄NF (1.0 M solution in THF, 0.39 mmol) in dry THF (1 mL) was stirred at room temperature. After 2.5 h, additional Bu₄NF (0.13 mmol) was added and the mixture was further stirred for 2 h. Work-up similar to that described above gave 17b (104 mg, 94%).

17b (1-βOH): ¹H NMR (CDCl₃) δ: 1.77 and 1.88 (each 1H, m), 2.07 (2H, m), 3.76 and 3.88 (each 1H, m), 4.00 (1H, dt, J=9.4, 3.1 Hz), 4.09 (1H, m), 4.55 (2H, s, CH₂Ph), 4.56, 4.62, 4.63 and 4.76 (each 1H, d, J=12.1 Hz, CH₂Ph), 7.27~7.51 (15H, m, arom H).

Mass m/z (%): 418 (M⁺, 0.2), 341 (1), 327 (15), 309 (1), 91 (100).

[Step 12a]: Compound 17a ⟶ Compound 18

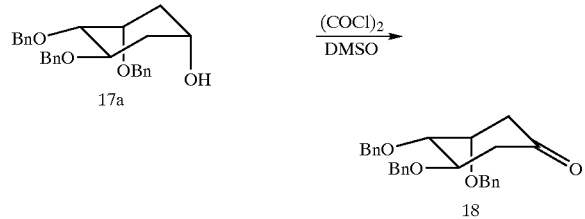

A solution of methyl sulfoxide (DMSO, 717 mg, 9.18 mmol) in dry CH₂Cl₂ (2 mL) was added slowly to a solution of oxalyl chloride (583 mg, 4.59 mmol) in dry CH₂Cl₂ (3 mL) at −78° C. The mixture was stirred for 5 min, and then a solution of 17a (1.60 g, 3.82 mmol) in dry CH₂Cl₂ (7 mL) was added dropwise. The reaction mixture was stirred for 15 min and treated with triethylamine (1.934 g, 19.1 mmol) for 30 min at −78° C. The cooling bath was removed, and the mixture was allowed to warm to room temperature, and then stirring was continued for 1 h. The reaction mixture was quenched with ice-water and extracted with CH₂Cl₂. The organic extract was washed with brine, dried over MgSO₄, and evaporated in vacuo. The residue was purified by chromatography on silica gel (30 g) using 15% AcOEt-hexane to afford 18 (1.50 g, 94%).

18: ¹H NMR (CDCl₃) δ: 2.48 (1H, dm, J=15 Hz), 2.62 (1H, dd, J=13.9, 4.5 Hz), 2.79 (1H, dd, J=15.0, 3.9 Hz), 2.87 (1H, dd, J=13.9, 10.5 Hz), 3.99 (2H, m, 4, 5-H), 4.06 (1H, ddd, J=10.3, 4.5, 2.3 Hz, 3-H), 4.41, 4.52, 4.53, 4.59, 4.70 and 4.86 (each 1H, d, J=12.0 Hz, CH₂Ph), 7.20~7.36 (15H, m, arom H).

Mass m/z (%): 416 (M⁺, 1), 325 (16), 308 (1), 217 (10), 91 (100).

[Step 12b]: Compound 17b ⟶ Compound 18

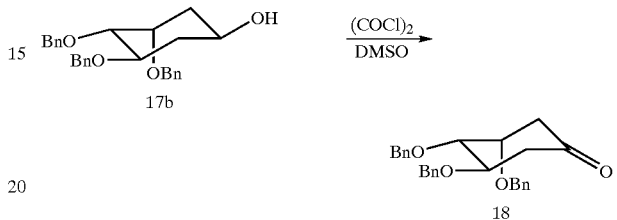

A solution of DMSO (46 mg, 0.59 mmol) in dry CH₂Cl₂ (200 μL) was added slowly to a solution of oxalyl chloride (38 mg, 0.30 mmol) in dry CH₂Cl₂ (300 μL) at −78° C. The mixture was stirred for 5 min, and then a solution of 17b (104 mg, 0.25 mmol) in dry CH₂Cl₂ (500 mL) was added dropwise. The reaction mixture was stirred for 15 min and treated with triethylamine (126 mg, 1.24 mmol) for 30 min at −78° C. The cooling bath was removed, and the mixture was allowed to warm to room temperature, and then stirring was continued for 1 h. Work-up similar to that described above afforded 18 (101 mg, 98%).

[Step 13]: Compound 18 ⟶ Compound 19

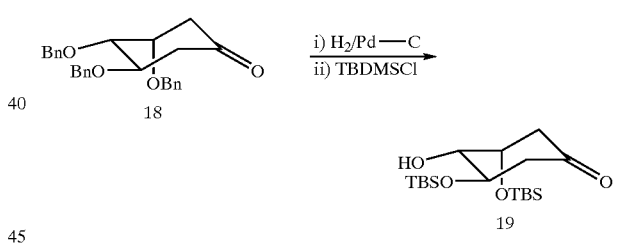

A mixture of 18 (713 mg, 1.71 mmol) and palladium, 10 wt % on carbon (142 mg) in EtOH (7 mL) was hydrogenolyzed under a atmospheric pressure of H₂ at room temperature. After vigorous stirring for 3 h, AcOEt (7 mL) was added and stirring was continued for additional 2.5 h. The reaction mixture was filtered through a pad of Celite and the filtrate was evaporated to dryness to yield the crude triol (270 mg).

A mixture of the crude triol (270 mg), triethylamine (693 mg, 6.85 mmol), 4-dimethylamionpyridine (105 mg, 0.86 mmol) and tert-butyldimethylsiyl chloride (774 mg, 5.14 mmol) in dry DMF (3.5 mL) was stirred at 0° C. for 4 h. The reaction mixture was poured into ice-water and extracted with AcOEt. The organic extract was washed with brine, dried over MgSO₄, and evaporated in vacuo. The residue was purified by chromatography on silica gel (35 g) using 10% AcOEt-hexane to give 19 (466 mg, 73%).

Intermediate triol: ¹H NMR (CDCl₃) δ: 2.28 (1H, dd, J=14.4, 7.7 Hz), 2.46 (1H, dd, J=14.3, 3.6 Hz), 2.53 (1H, dd, J=14.4, 6.3 Hz), 2.66 (1H, dd, J=14.4, 3.6 Hz), 3.75 (1H, d, J=5.2 Hz), 4.03 (1H, m), 4.12 (1H, br. Signal).

Mass m/z (%): 146 (M+, 2), 128 (3), 110 (2), 87 (63), 60 (100).

19: $^1$H NMR (CDCl$_3$) δ: 0.07 (6H, s, Si—CH$_3$), 0.086 and 0.092 (each 3H, s, Si—CH$_3$), 0.86 and 0.90 (each 1H, s, Si-tBu), 2.25 (1H, dm, J=14.4 Hz), 2.46 (1H, ddm, J=13.8, 4.9 Hz), 2.60 (1H, dd, J=13.8, 9.8 Hz), 2.63 (1H, s, OH), 2.77 (1H, dd, J=14.4, 3.5 Hz), 3.80 (1H, m, 4-H), 4.28 (2H, m, 3, 5-H).

Mass m/z (%): 374 (no M+), 359 (2), 341 (2), 317 (61), 299 (12), 185 (95), 143 (100).

$^1$H NMR and Mass spectra of 19 were in agreement with those reported. Sicinski R R, Perlman K L, DeLuca H F, *J. Med. Chem.* 1994, 37, 3730–3738.

Example 4

(See Scheme IV):

The synthesis of 2-substituted phosphine oxide 23a,b from 19 was performed according to the published procedure (Sicinski R R, Perlman K L, DeLuca H F, *J. Med. Chem.* 1994, 37, 3730–3738).

[Step 14]: Compound 19 ⟶ Compound 20

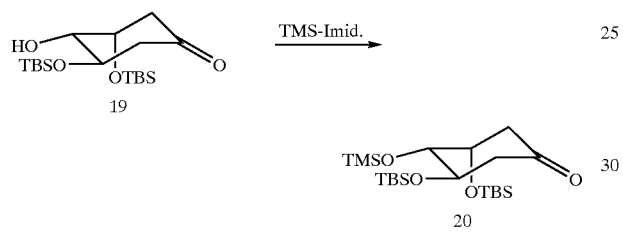

To a solution of 19 (1.12 g, 2.99 mmol) in dry CH$_2$Cl$_2$ (10 mL) was added 1-(trimethylsilyl)imidazole (839 mg, 5.98 mmol) at 0° C. After being stirred for 2 h at the same temperature, water (1.5 mL) was add and the mixture was stirred for 30 min. The reaction mixture was extracted with CH$_2$Cl$_2$. The organic extract was washed with brine, dried over MgSO$_4$, and evaporated in vacuo. The residue was purified by chromatography on silica gel (30 g) with 3% AcOEt hexane to afford 20 (1.32 g, 99%).

20: $^1$H NMR (CDCl$_3$) δ: 0.05 (6H, s, Si—CH$_3$), 0.06 and 0.07 (each 3H, s, Si—CH$_3$), 0.16 (9H, s, Si—CH$_3$), 0.86 and 0.89 (each 1H, s, Si-tBu), 2.17 (1H, dm), 2.36 (1H, dd, J=13.7, 4.4 Hz), 2.73 (2H, m), 3.80 (1H, m, 4-H), 4.03 (1H, m), 4.24 (1H, ddd, J=10.6, 4.5, 2.3 Hz).

Mass m/z (%): 446 (no M+), 431 (7), 389 (100), 315 (4), 299 (99), 257 (57), 225 (22).

[Step 15]: Compound 20 ⟶ Compound 21a, b

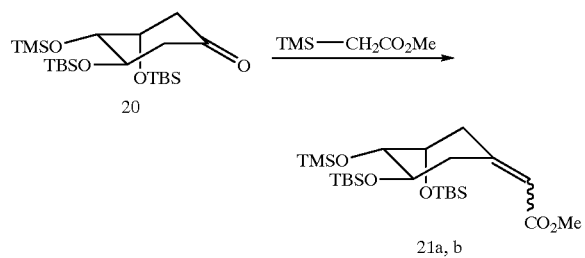

To a stirred solution of diisopropylamine (601 mg, 5.94 mmol) in dry THF (3 mL) was added butyllithium (BuLi, 1.4 M solution in hexane, 4.24 mL, 5.94 mmol) at −78° C. The mixture was stirred for 15 min and methyl (trimethylsilyl) acetate (869 mg, 5.94 mmol) was added. After being stirred for 10 min at −78° C., a precooled solution of 20 (1.32 g, 2.95 mmol) in dry THF (5 mL) was slowly added. The reaction mixture was stirred for 1.5 h at the same temperature and allowed to warm to 0° C. The mixture was quenched with addition of saturated aqueous ammonium chloride (NH$_4$claim) solution, and extracted with AcOEt. The organic extract was washed with brine, dried over MgSO$_4$, and evaporated to dryness. The residue was chromatographed on silica gel (35 g) using 3% AcOEt-hexane to give 21 (1.47 g, 99%) as an unseparable mixture of two isomers due to newly generated double bond isomerism.

21a (major): $^1$H NMR (CDCl$_3$) δ: 0.04, 0.05, 0.075 and 0.08 (each 3H, s, Si—CH$_3$), 0.13 (9H, s, Si—CH3), 0.86 and 0.887 (each 9H, Si-tBu), 2.00 (1H, dd, J=13.5, 4.7 Hz), 2.60 (1H, dm, J=13.5 Hz), 2.72 and 3.28 (each 1H, m), 3.62 (1H, m), 3.68 (3H, s, OCH$_3$), 3.86 (1H, m), 3.95 (1H, m, 3-H), 5.62 (1H, s).

21b (minor): $^1$H NMR (CDCl$_3$) δ: 0.04, 0.05 (each 3H, s, Si—CH$_3$), 0.06 (6H, s, Si—CH$_3$), 0.13 (9H, s, Si—CH$_3$), 0.84 and 0.892 (each 9H, Si-tBu), 2.12 (1H, dd, J=13.6, 3.8 Hz), 3.66 (3H, s, OCH$_3$), 3.98 (1H, m), 5.70 (1H, s).

21a and 21b: Mass m/z (%): 502 (no M+), 487 (4), 445 (90), 413 (9), 385 (4), 355 (8), 313 (50), 281 (100).

[Step 16]: Compound 21a, b ⟶ Compound 22a, b

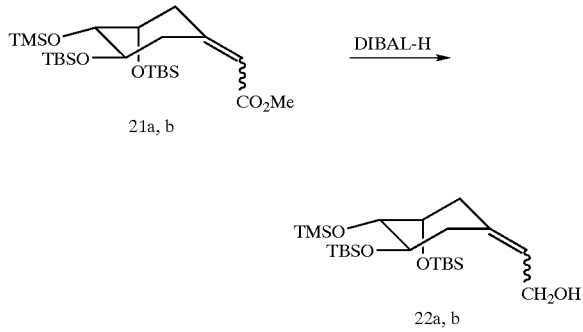

To a solution of 21a,b (1.47 g, 2.93 mmol) in dry toluene (10 mL) was added diisobutylaluminum hydride (1 M solution in toluene, 11.7 mL, 11.7 mmol) at −78° C. After being stirred for 1 h at the same temperature, the reaction mixture was quenched with a saturated aqueous sodium potassium tartarate solution, and extracted with AcOEt. The AcOEt extract was washed with water, dried over MgSO$_4$, and evaporated in vacuo. The residue was purified by chromatography on silica gel (35 g) using 10% AcOEt-hexane to afford 22a,b (1.36 g, 98%) as a mixture of two isomers.

22a (major): $^1$H NMR (CDCl$_3$) δ: 0.04, 0.05, 0.058 and 0.07 (each 3H, s, Si—CH$_3$), 0.13 (9H, s, Si—CH$_3$), 0.87 and 0.889 (each 9H, Si-tBu), 1.93 (1H, dd, J=13.6, 5.4 Hz), 2.24 and 2.38 (each 1H, m), 2.50 (1H, br. D, J=13.0 Hz), 3.56 (1H, m), 3.79 (1H, m), 3.89 (1H, m), 4.12 (2H, m), 5.44 (1H, t, J=7.1 Hz).

22b (minor): $^1$H NMR (CDCl$_3$) δ: 0.058 and 0.063 (each 6H, s, Si—CH$_3$), 0.13 (9H, s, SiCH$_3$), 0.87 and 0.892 (each 9H, Si-tBu), 2.06 (1H, dd, J=13.6, 4.0 Hz), 3.62 (1H, m), 4.05 (1H, m), 5.57 (1H, t, J=7.0 Hz).

22a and 22b: Mass m/z (%): 474 (no M+), 441 (2), 399 (28), 349 (5), 325 (21), 307 (23), 285 (20), 253 (69), 235 (52), 73 (100).

[Step 17]: Compound 22a, b ⟶ Compound 23a, b

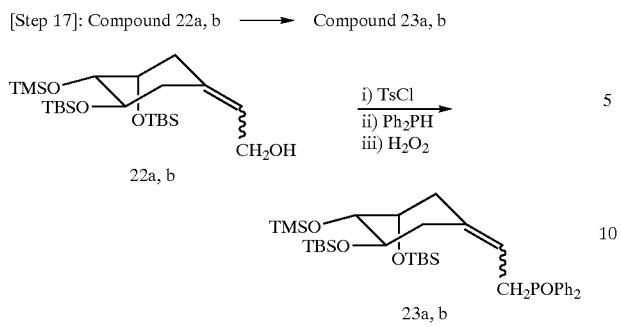

To a solution of 22a,b (1.35 g, 2.84 mmol) in dry THF (10 mL) was added n-BuLi (1.4 M solution in hexane, 3.12 mmol) at 0° C., a solution of freshly recrystallized p-toluenesulfonyl chloride (0.595 g, 3.12 mmol) in dry THF (2 mL) was added dropwise, and the mixture was stirred for 5 min. n-BuLi (1.4 M solution in hexane, 4.26 mol) was added to a stirred, cold (0° C.) solution of diphenylphosphine (768 mg, 4.2 mmol) in dry THF (3 mL) and the mixture turned orange in color. This orange solution was slowly added to the above tosylate in THF solution and the mixture was stirred for 30 min at 0° C. Water (200 μL) was added and the solvent was evaporated to dryness. The residue was dissolved in $CH_2Cl_2$ (7 mL) and to this solution was added 100% hydrogen peroxide (9 mL). The mixture was stirred for 1 h at 0° C. and $CH_2Cl_2$ layer was separated. The organic phase was successively washed with cold 2N sodium sulfite, water and brine, and dried over $MgSO_4$. After evaporation of the solvent, the resulting residue was purified by chromatography on silica gel (80 g) with 40% AcOEt-hexane to yield 23a,b (1.47 g, 79%) as a mixture of two isomers.

23a (major): $^1$H NMR (CDCl$_3$) δ: −0.02, 0.00, 0.01 and 0.03 (each 3H, s, Si—CH$_3$), 0.13 (9H, s, Si—CH$_3$), 0.82 and 0.87 (each 9H, S I-tBu), 1.86 (1H, m), 1.99 (1H, m), 2.08 (1H, m), 2.42 (1H, br. D, J=13.7 Hz), 3.10 (2H, m), 3.51 (1H, m), 3.72 (1H, m), 3.82 (1H, m), 5.24 (1H, m).

23b (minor): Most of the signals were overlapped with the major product 23a.

23a and 23b: Mass m/z (%): 658 (no M$^+$), 643 (4), 601 (100), 526 (19), 511 (4), 469 (48), 437 (15), 394 (9).

SCHEME I

Synthesis of 2-deoxy-glucose derivative 7 from D-glucose

[Method A]

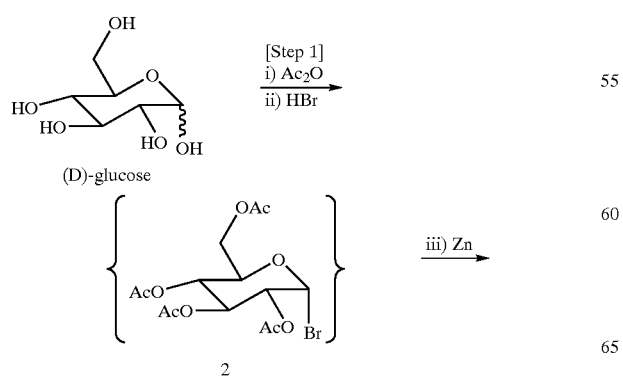

SCHEME II

Synthesis of 2-deoxy-glucose derivative 7 from D-glucose

[Method B]

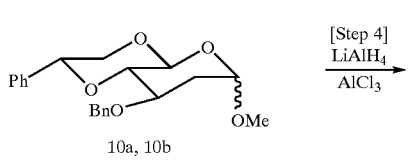
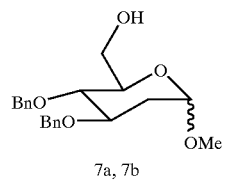
SCHEME III
Synthesis of 4-substituted phosphine oxide 23a, 23b from 7
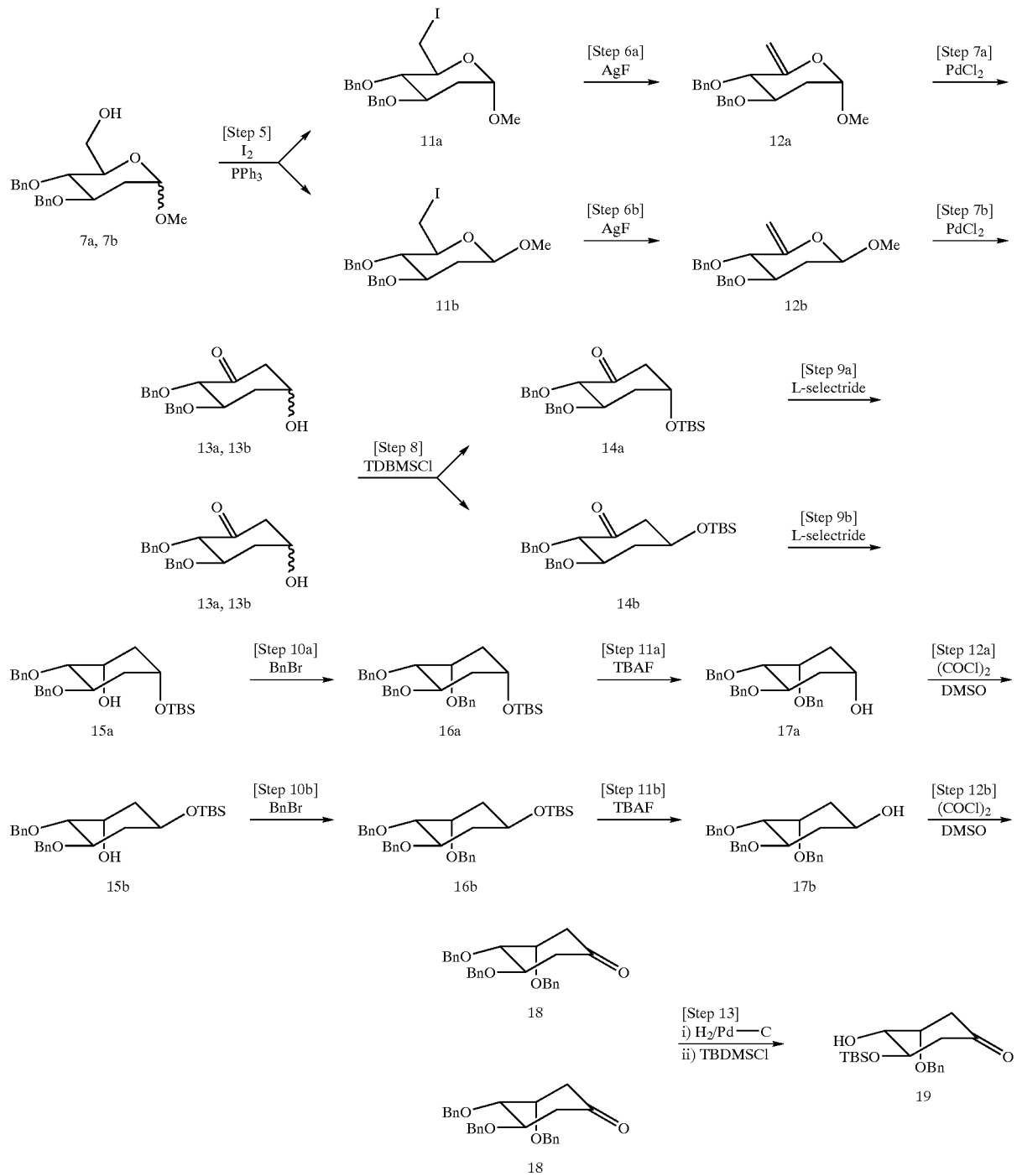

SCHEME IV

Synthesis of phosphine oxide 23a, 23b from 19

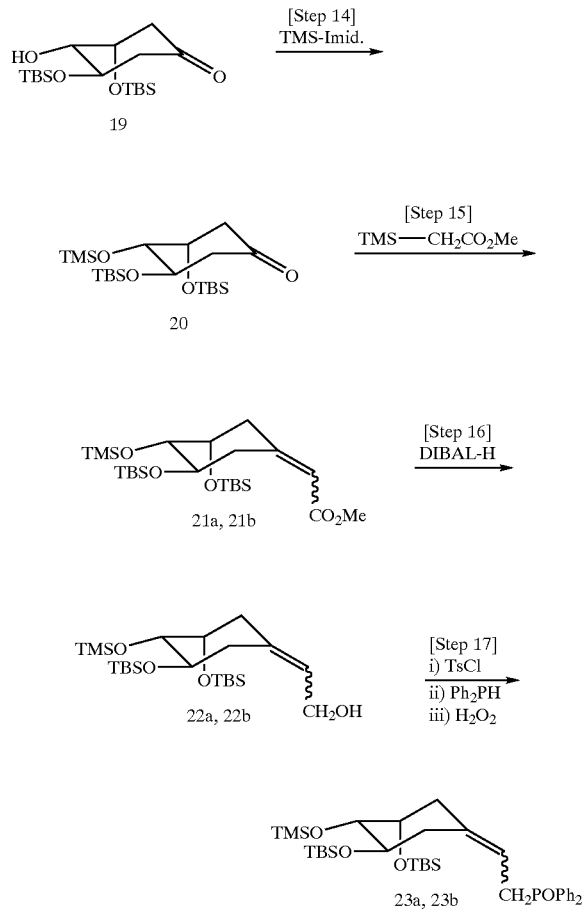

We claim:

1. A compound having the formula

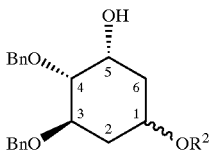

where Bn is a benzyl group, and $R^2$ is a hydroxy protecting group.

2. A compound having the formula

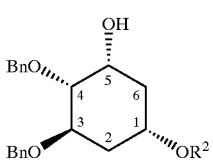

where Bn is a benzyl group, and $R^2$ is a hydroxy protecting group.

3. The compound of claim 2 wherein $R^2$ is tert-butyldimethylsilyl.

4. A compound having the formula

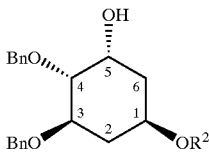

where Bn is a benzyl group, and $R^2$ is a hydroxy protecting group.

5. The compound of claim 4 wherein $R^2$ is tert-butyldimethylsilyl.

* * * * *